US011399787B2

(12) United States Patent
Lewis et al.

(10) Patent No.: US 11,399,787 B2
(45) Date of Patent: Aug. 2, 2022

(54) METHODS AND SYSTEMS FOR CONTROLLING AN ADAPTIVE CONTRAST SCAN

(71) Applicant: GE Precision Healthcare LLC, Milwaukee, WI (US)

(72) Inventors: Chelsey Lewis, Waukesha, WI (US); Michael Sarju Vaz, Milwaukee, WI (US); Bradley J. Gabrielse, Brookfield, WI (US); Maud Bonnard, Brookfield, WI (US); Ryan C. Forbes, Waukesha, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 189 days.

(21) Appl. No.: 16/698,890

(22) Filed: Nov. 27, 2019

(65) Prior Publication Data

US 2021/0153827 A1    May 27, 2021

(51) Int. Cl.
*A61B 6/00*    (2006.01)
*A61B 6/03*    (2006.01)
*G06F 3/0482*    (2013.01)
*G06F 3/04847*    (2022.01)

(52) U.S. Cl.
CPC .............. *A61B 6/465* (2013.01); *A61B 6/032* (2013.01); *A61B 6/463* (2013.01); *A61B 6/504* (2013.01); *G06F 3/0482* (2013.01); *G06F 3/04847* (2013.01)

(58) Field of Classification Search
CPC ......... A61B 6/465; A61B 6/032; A61B 6/463; A61B 6/504; G06F 3/0482; G06F 3/04847
See application file for complete search history.

(56) References Cited

U.S. PATENT DOCUMENTS

| 5,400,378 | A | 3/1995 | Toth |
| 6,023,494 | A | 2/2000 | Senzig et al. |
| 6,236,706 | B1 | 5/2001 | Hsieh |
| 6,256,368 | B1 | 7/2001 | Hsieh et al. |

(Continued)

FOREIGN PATENT DOCUMENTS

CN    101277648 A    10/2008

OTHER PUBLICATIONS

"The ONE Guides—4D Neurological Imaging," Cannon Medical Systems USA Website, Available Online at https://us.medical.canon/download/aq-one-club-guide-4d-neuro-imaging, Available Online at Early as Jan. 2010, 16 pages.

(Continued)

*Primary Examiner* — Tadesse Hailu
(74) *Attorney, Agent, or Firm* — McCoy Russell LLP

(57) ABSTRACT

Methods and systems are provided for adaptive scan control. In one embodiment, a method for a computing device communicatively coupled to an imaging system includes, selecting a scan protocol, displaying an adaptive scan protocol graphical user interface (GUI) on a display device coupled to the computing device, adjusting one or more parameters of the scan protocol in response to user input to the adaptive scan protocol GUI, updating a visual representation of the scan protocol displayed via the adaptive scan protocol GUI in correspondence to the adjustment of the one or more parameters of the scan protocol, and storing the adjusted scan protocol in memory of the computing device.

17 Claims, 6 Drawing Sheets

(56) References Cited

U.S. PATENT DOCUMENTS

| | | | |
|---|---|---|---|
| 6,891,918 | B2 | 5/2005 | Drummond et al. |
| 7,145,982 | B2 | 12/2006 | Ikeda et al. |
| 7,983,460 | B2 | 7/2011 | Licato et al. |
| 9,327,143 | B2 | 5/2016 | Gillece et al. |
| 9,486,176 | B2 | 11/2016 | Goyal |
| 9,517,042 | B2 | 12/2016 | Hsieh et al. |
| 9,622,717 | B2 | 4/2017 | Londt et al. |
| 10,349,909 | B2 | 7/2019 | Okerlund et al. |
| 2003/0236458 | A1* | 12/2003 | Hochman ............... A61B 5/418 600/431 |
| 2007/0214017 | A1* | 9/2007 | Profio ..................... G16H 30/20 705/3 |
| 2010/0217617 | A1* | 8/2010 | Springorum ........... G16H 50/20 705/2 |
| 2012/0179006 | A1* | 7/2012 | Jansen .................. A61B 5/1455 600/301 |
| 2014/0098931 | A1* | 4/2014 | Profio ..................... A61B 6/465 378/19 |
| 2014/0098932 | A1* | 4/2014 | Profio ..................... A61B 6/032 378/19 |
| 2014/0098933 | A1* | 4/2014 | Profio ..................... A61B 6/465 378/19 |
| 2016/0092748 | A1* | 3/2016 | Koktava .............. G06K 9/6201 382/128 |
| 2017/0086772 | A1* | 3/2017 | Vaz .......................... A61B 6/54 |
| 2017/0209113 | A1 | 7/2017 | Jackson et al. |
| 2018/0049714 | A1 | 2/2018 | Nett |
| 2019/0231224 | A1* | 8/2019 | Rupcich .................... G06T 7/97 |
| 2019/0231288 | A1 | 8/2019 | Profio et al. |

OTHER PUBLICATIONS

Hinzpeter, R. et al., "CT Angiography of the Aorta: Contrast Timing by Using a Fixed versus a Patient-specific Trigger Delay," University of Zurich Open Repository and Archive Website, Available Online at https://www.zora.uzh.ch/id/eprint/170529/1/radiol.2019182223.pdf, Available as Early as May 2019, 10 pages.

Lewis, C. et al., "Methods and Sytems for Protocol Management," U.S. Appl. No. 16/553,028, filed Aug. 27, 2019, 59 pages.

Vaz, M. et al., "Methods and Systems for Timing a Second Contrast Bolus," U.S. Appl. No. 16/672,261, filed Nov. 1, 2019, 84 pages.

Vaz, M. et al., "Methods and Systems for an Adaptive Multi-Phase Angiography Scan," U.S. Appl. No. 16/672,281, filed Nov. 1, 2019, 85 pages.

Vaz, M. et al., "Methods and Systems for an Adaptive Five-Zone Perfusion Scan," U.S. Appl. No. 16/672,314, filed Nov. 1, 2019, 85 pages.

Vaz, M. et al., "Methods and Systems for a Single-Bolus Angiography and Perfusion Scan," U.S. Appl. No. 16/672,336, filed Nov. 1, 2019, 85 pages.

Vaz., M. et al., "Methods and Systems for an Adaptive Four-Zone Perfusion Scan," U.S. Appl. No. 16/672,350, filed Nov. 1, 2019, 85 pages.

Lewis, C., "An Ornamental Design for a Display Screen or Portion Therof With Graphical User Interface," U.S. Appl. No. 29/715,166, filed Nov. 27, 2019, 14 pages.

* cited by examiner

METHODS AND SYSTEMS FOR CONTROLLING AN ADAPTIVE CONTRAST SCAN

FIELD

Embodiments of the subject matter disclosed herein relate to non-invasive diagnostic imaging, and more particularly, to real-time adaptive contrast imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

For emergency room (ER) stroke management, time is critical to determine a proper course of treatment. For every minute a large vessel ischemic stroke is untreated, the average patient loses 1.9 million neurons. For each hour in which a treatment fails, the patient loses as many neurons as it does in almost 3.6 years of normal aging. Current standards of care for acute stroke typically include one or more CT scans in order to guide subsequent treatment decisions. Due to the time-sensitive nature of acute stroke care, it is desirable that these CT scans be performed as quickly as possible.

BRIEF DESCRIPTION

In one embodiment, a method for a computing device communicatively coupled to an imaging system includes selecting a scan protocol, displaying an adaptive scan protocol graphical user interface (GUI) on a display device coupled to the computing device, adjusting one or more parameters of the scan protocol in response to user input to the adaptive scan protocol GUI, updating a visual representation of the scan protocol displayed via the adaptive scan protocol GUI in correspondence to the adjustment of the one or more parameters of the scan protocol, and storing the adjusted scan protocol in memory of the computing device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
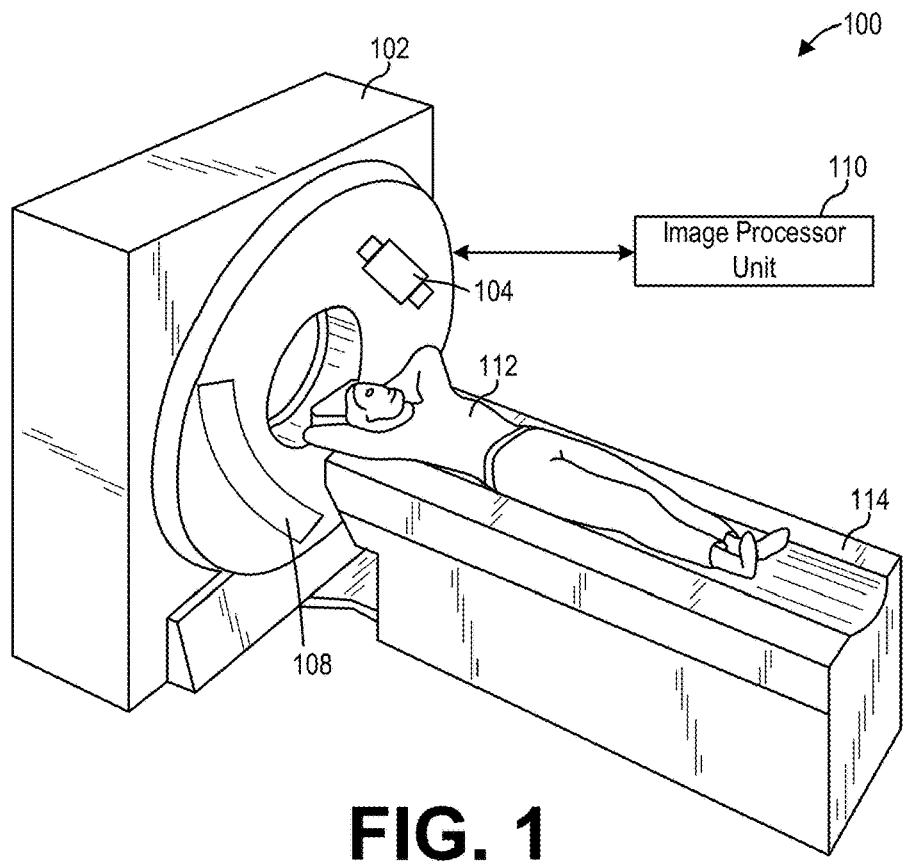
FIG. 1 shows a pictorial view of an imaging system, according to an embodiment.

Some diagnostic imaging protocols, such as protocols to diagnose acute stroke in a patient, include one or more contrast scans, where a contrast agent is administered to the patient prior to the diagnostic imaging scan. Example contrast scans include a computed tomography (CT) angiography (CTA) scan and a CT perfusion (CTP) scan. Contrast scans, when used during acute stroke care, may be used by clinicians as a tool to decide if a particular patient will benefit from endovascular thrombectomy. Due to the time sensitive nature of acute stroke care and the scan and reconstruction duration of a contrast scan, the contrast scan may be performed as soon as a patient arrives at a medical facility, often before patient information and any recent patient hemodynamic information is available, and the contrast scans may be performed as quickly as possible in order to expedite patient diagnosis. However, without recent patient hemodynamic information, contrast scans are typically performed according to fixed protocols that may be longer or shorter than necessary for a given patient. Further, the cognitive load placed on the scan machine operator/technologist during the time of the contrast scan may be relatively high, and any adaptations to predefined contrast scan protocols made on the fly as patient hemodynamic information is learned may further add to the cognitive load, thereby increasing the likelihood rescans may have to performed.

Thus, as will be described in more detail below, personalized, adaptive contrast scans may be performed when no prior knowledge of the patient's contrast agent response is available. The adaptive contrast scans described herein may adjust aspects of the scan parameters (e.g., temporal acquisition rate) at one or more time points (referred to as zone transitions) that are identified based on the patient's individual contrast agent kinetics, such as the amount of time from contrast agent injection until various inflection points/time points of interest on the patient's arterial inflow function (AIF) curve and venous outflow function (VOF) curve, including but not limited to the venous peak and venous return to baseline.

Each type of contrast scan (e.g., a CTA, a CTP, and/or a CTA in a CTP) may be carried out according to a scan prescription that is set based on a predefined scan protocol. A lead technologist, a radiologist, and/or one or more additional clinicians/administrators may set various parameters for each scan protocol in advance via an adaptive scan protocol graphical user interface (GUI). The adaptive scan protocol GUI may allow the lead technologist and/or other personnel to divide the contrast scan into zones, and set different scan parameters (such as temporal acquisition rate, also known as temporal sampling rate, x-ray source current, etc.) for each selected zone. The timing of when each zone is to occur may be set by the lead technologist based on patient events, such as the individual patient's hemodynamics/contrast agent response, which may be determined on the fly as the contrast scan progresses, or may be determined based on prior information (e.g., a timing bolus or prior contrast scan). For some contrast scan protocols that include a secondary scan performed with a primary scan, such as CTA in CTPs, the adaptive scan protocol GUI may also allow the lead technologist to set the timing for the acquisitions of the secondary scan relative to the primary scan.

During execution of a selected contrast scan protocol to image a patient with an imaging system (e.g., CT system), the operator/technologist of the imaging system may select the appropriate predefined scan protocol. The adaptive scan protocol GUI may be displayed to the operator, allowing the operator to confirm or, if necessary, change the preset scan parameters. If prior information is available, the operator may provide an indication to load the prior information, and a scan prescription may be determined for carrying out the contrast scan based on the prior information and the selected scan protocol. If no prior information is available, the scan prescription may be adapted as the contrast scan progresses based on the patient information that is collected during the scan. The progress of the scan may be displayed via a run-time GUI, including (at least in some examples) a visual representation of the scan prescription in the form of a real-time, personalized representation of the patient's contrast agent response curve.

To determine the patient's individual contrast agent kinetics, a contrast agent signal may be measured during an initial portion of the contrast scan, and the contrast signal may comprise a measured contrast level in a monitoring region of the patient (e.g., a brain of the patient, an artery of the patient, a vein of the patient, etc.). This contrast agent signal may be entered as input to a machine learning (ML) model that may output an estimated arterial inflow function (AIF) curve, an estimated tissue uptake curve (TUC), and/or an estimated venous outflow function (VOF) curve (and/or time points of interest from the AIF and VOF curves, such as an arterial peak, a venous peak, and/or a venous return to baseline). Based on the output of the ML model, the timing of the one or more zone transitions may be identified and adjustments to the scan parameters (e.g., temporal sampling rate) may be made at the zone transitions. In doing so, patient x-ray radiation dose may be reduced and/or scan duration may be shortened while still acquiring high quality diagnostic images to support patient diagnosis.

Figure 2:
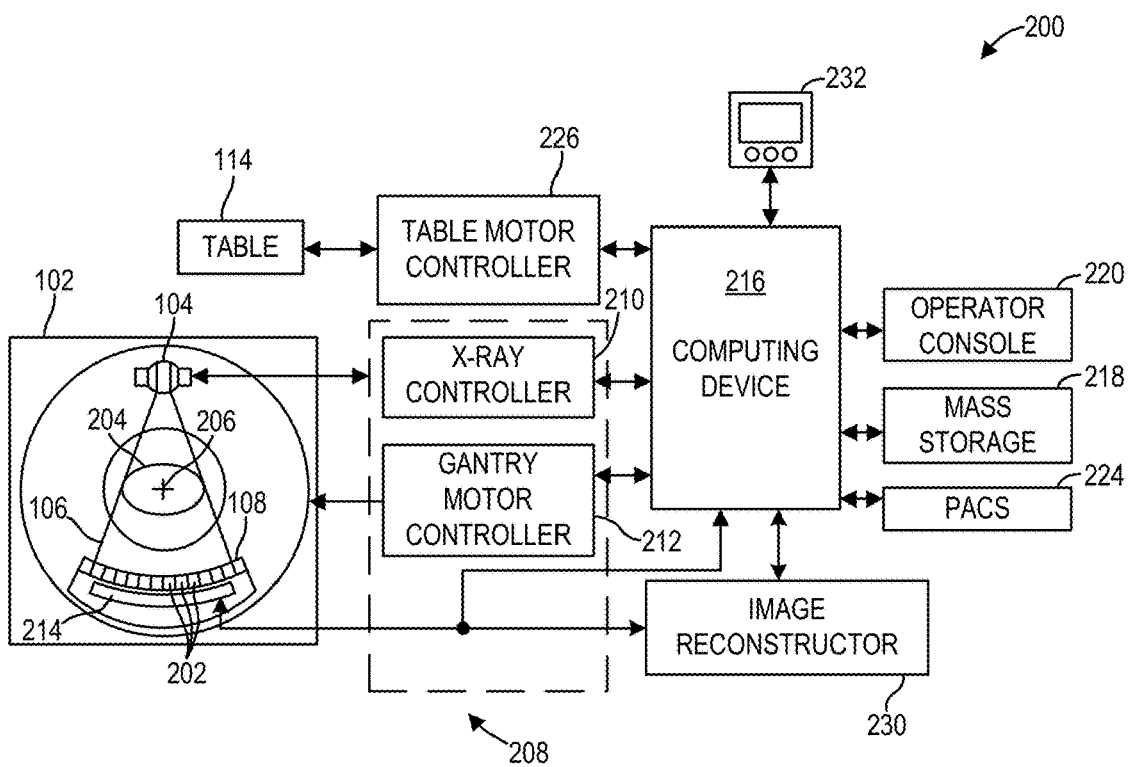
FIG. 2 shows a block schematic diagram of an exemplary imaging system, according to an embodiment.
Figure 3:
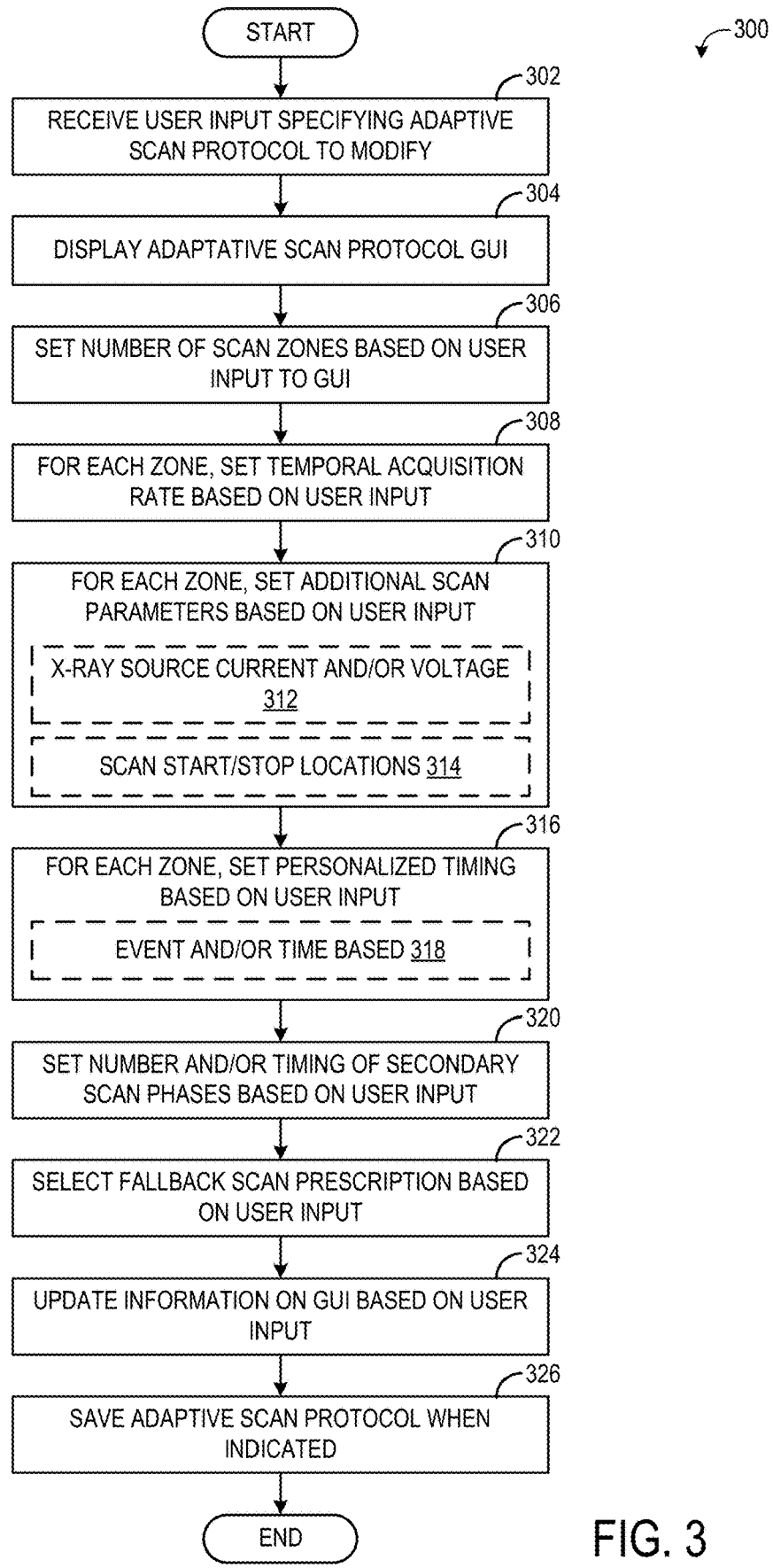
FIG. 3 is a flow chart illustrating a method for setting adaptive contrast scan settings in advance via an adaptive scan protocol graphical user interface (GUI)
Figure 4:
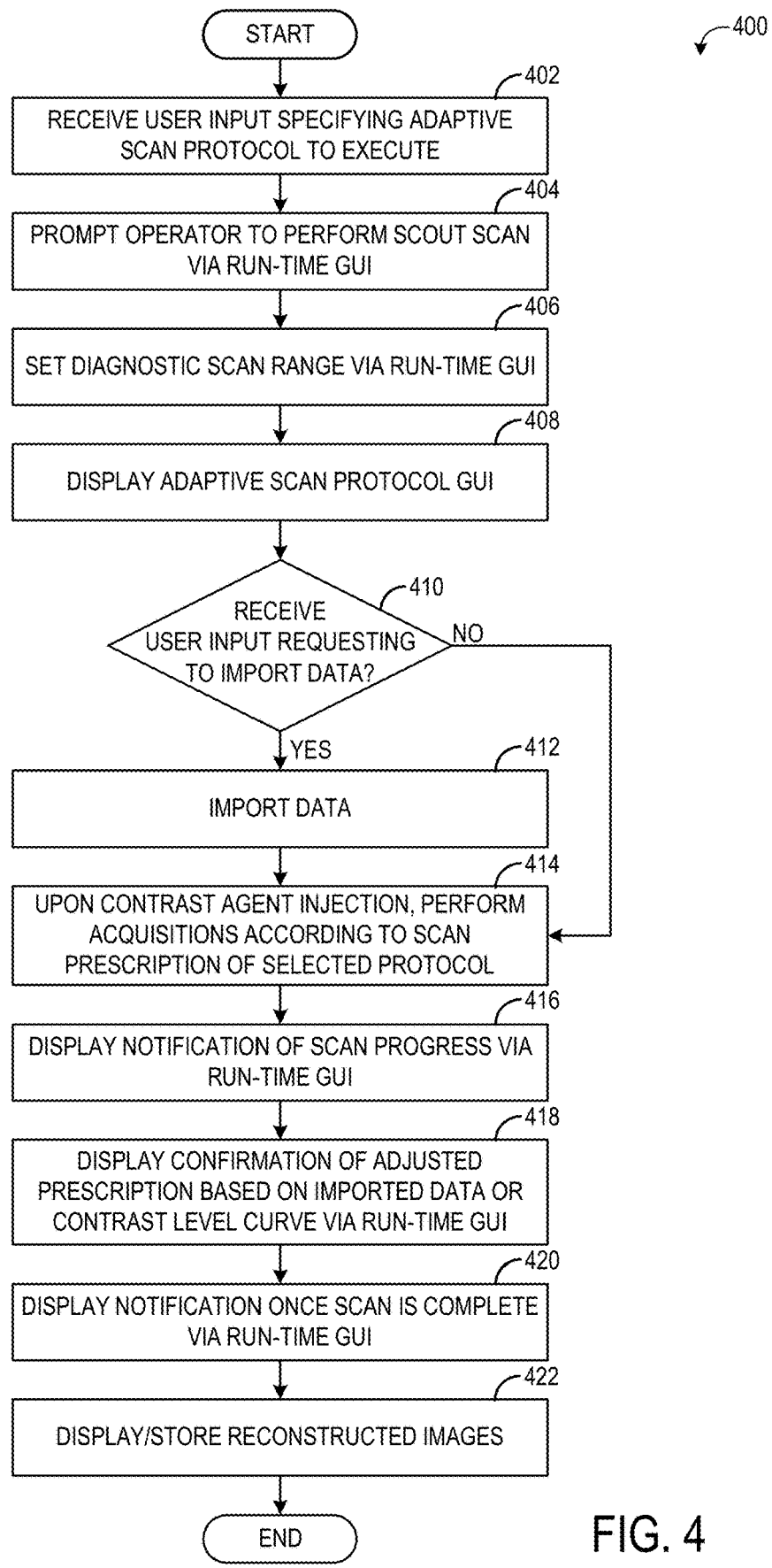
FIG. 4 is a flow chart illustrating a method for executing an adaptive contrast scan on a subject.
Figure 5:
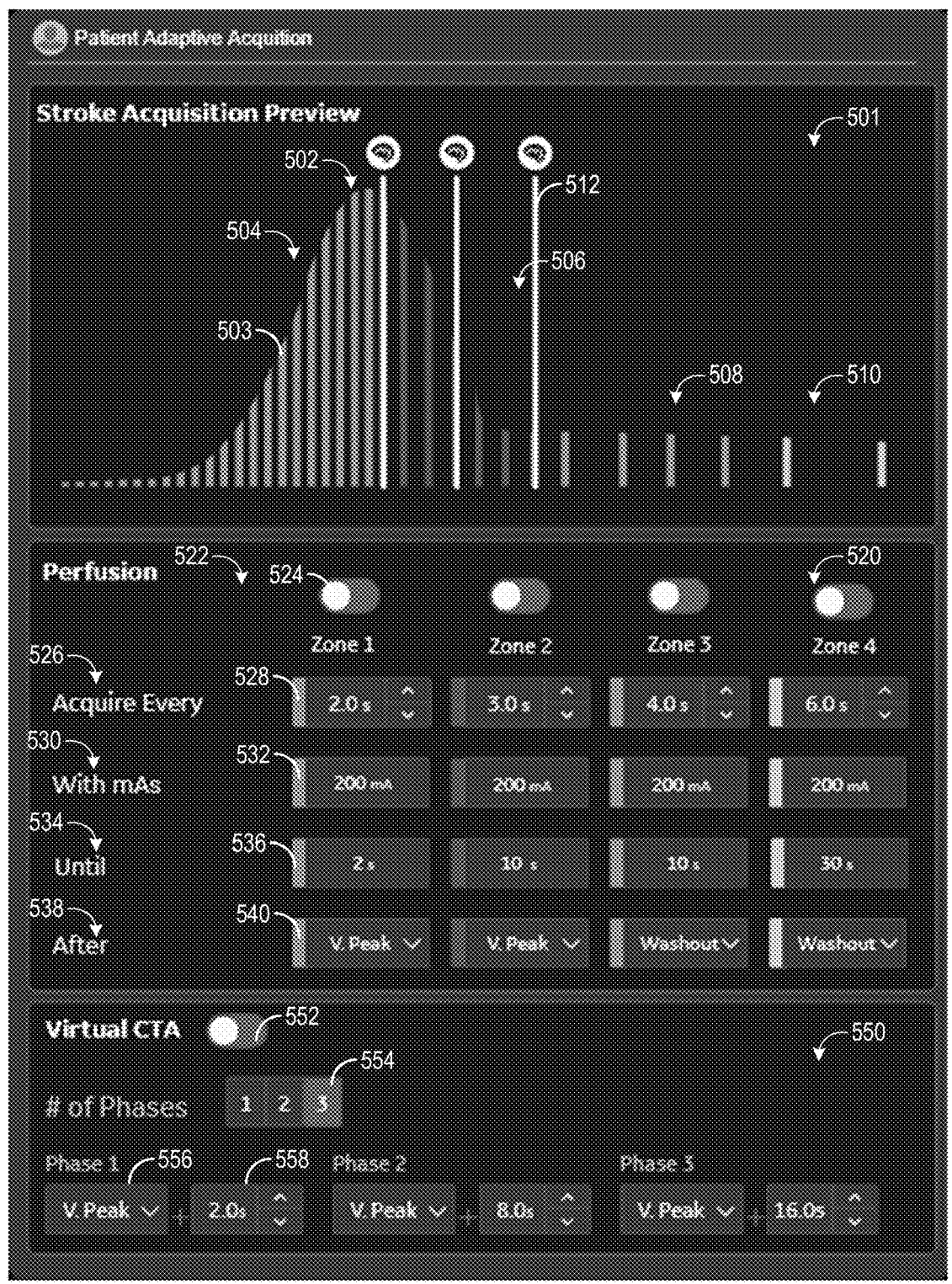
FIGS. 5 and 6 show an example of an adaptive scan protocol GUI.
Figure 6:
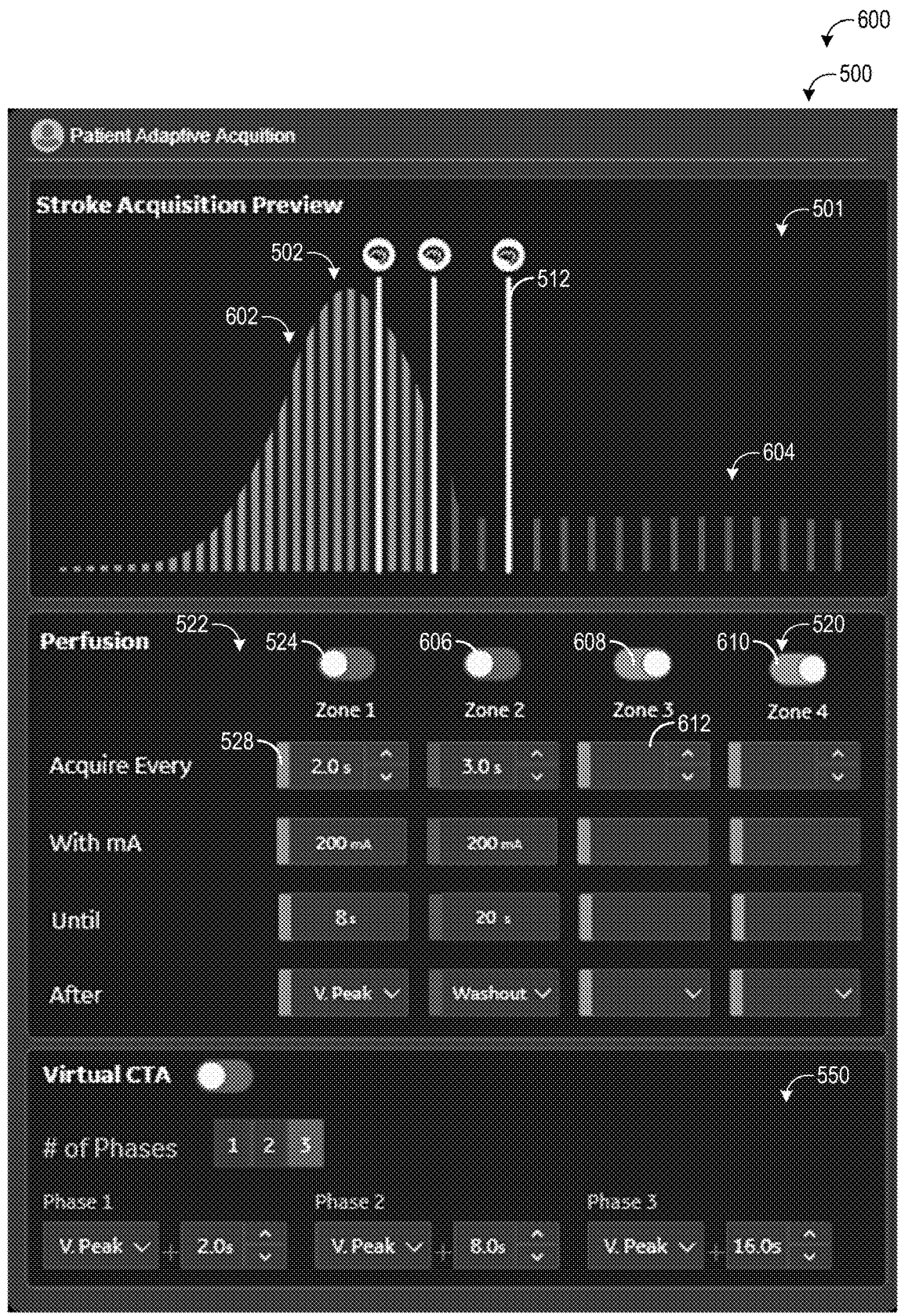
Figure 7:
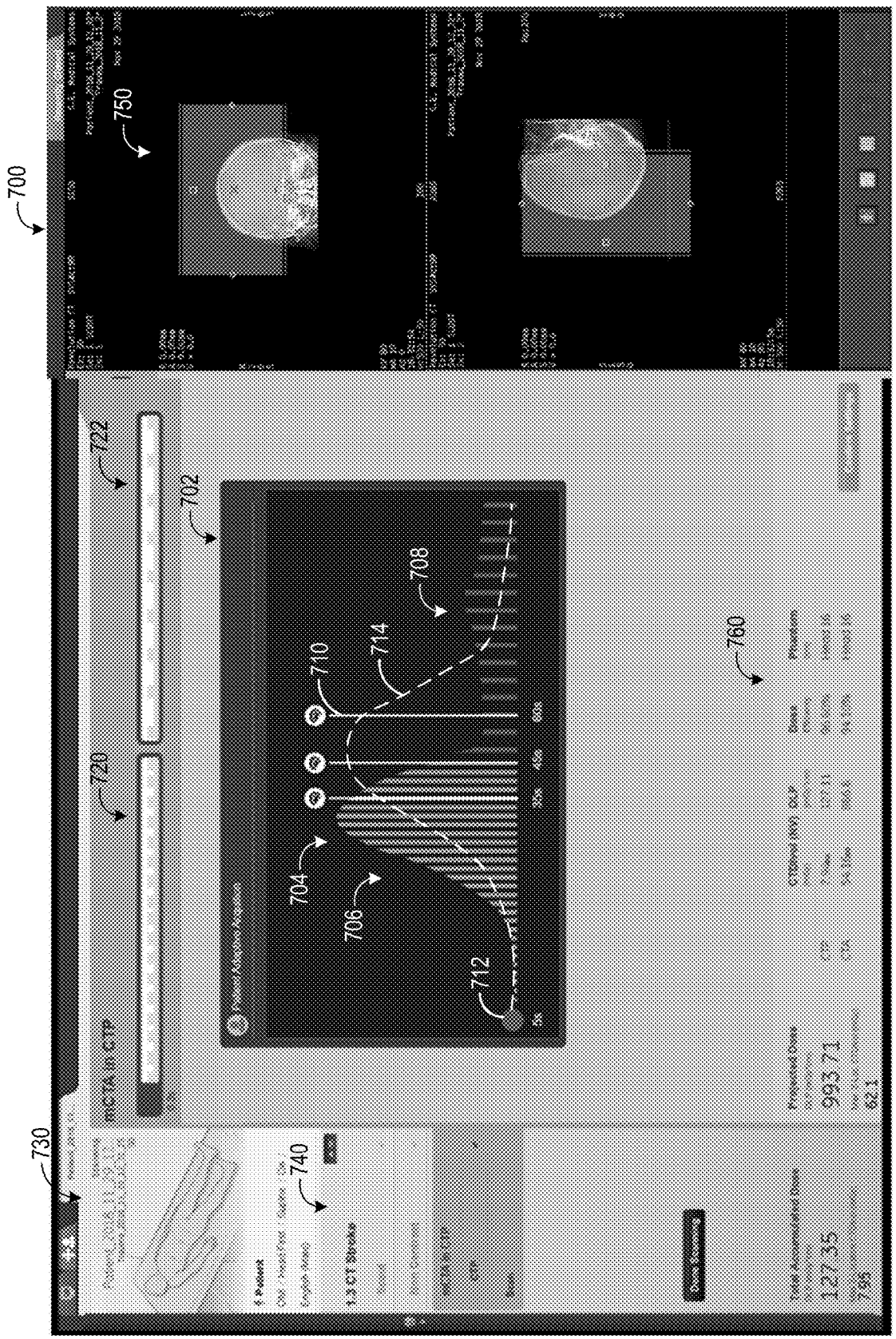
FIG. 7 shows an example of an adaptive scan run-time GUI.

An example of a computed tomography (CT) imaging system that may be used to perform the contrast scans in accordance with the present techniques is provided in FIGS. 1 and 2. One or more contrast scan protocols may be defined in advance via an adaptive contrast scan GUI, according to the method shown in FIG. 3. During execution of a selected contrast scan protocol, the contrast scan may be carried out according to the method of FIG. 4. Example adaptive scan protocol GUIs that may be displayed during the execution of the method of FIG. 3 are shown in FIGS. 5 and 6. An example run-time GUI that may be displayed during the execution of the method of FIG. 4 is shown in FIG. 7.

Though a CT system is described by way of example, it should be understood that the present techniques may also be useful when applied to images acquired using other imaging modalities, such as x-ray imaging systems, magnetic resonance imaging (MRI) systems, positron emission tomography (PET) imaging systems, single-photon emission computed tomography (SPECT) imaging systems, ultrasound imaging systems, and combinations thereof (e.g., multi-modality imaging systems, such as PET/CT, PET/MR or SPECT/CT imaging systems). The present discussion of a CT imaging modality is provided merely as an example of one suitable imaging modality. Further, while the present techniques may be discussed herein with respect to head/neck scans such as acute stroke scan protocols, the present techniques may be applied during other contrast scan protocols, such as cardiac scans, liver scans, etc.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the x-ray beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/ write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the method described below with reference to FIGS. 3 and 4) described further herein may be stored as executable instructions in non-transitory memory on a computing device (or controller) in imaging system 200. In an embodiment, computing device 216 may include the instructions in non-transitory memory, and may apply the methods described herein, at least in part, set contrast scan protocols, to measure AIF or TUC signals from a plurality of reconstructed images after receiving the reconstructed images from image reconstructor 230, and adapt scan prescriptions on the fly based on the measured AIF or TUC signals. In other embodiments, image reconstructor 230 may include such executable instructions in non-transitory memory, and may apply the methods described herein to adaptively plan and control contrast scans. In yet another embodiment, the methods and processes described herein may be distributed across image reconstructor 230 and computing device 216.

In one embodiment, the display 232 allows the operator to evaluate the imaged anatomy, view measured and/or estimated AIF and VOF curves, trigger aspects of the contrast scans, set scan protocols, and the like. The display 232 may also allow the operator to select a region of interest (ROI) and/or request patient information, for example, via a graphical user interface (GUI) for a subsequent scan or processing.

FIG. 3 shows a flow chart illustrating a method 300 for defining a contrast scan protocol. Method 300 is described with respect to the system and components described above with respect to FIGS. 1-2 but could be carried out with other systems/components without departing from the scope of this disclosure. Method 300 may be carried out according to instructions stored in non-transitory memory of a computing device (e.g., computing device 216 of FIG. 2). Method 300 may include the selection/adjustment of various parameters for one or more contrast scan protocols. Thus, method 300 may be performed in response to authenticating an authorized personnel, such as a lead technologist, radiologist, hospital administrator, etc.

At 302, a user input specifying an adaptive scan protocol to modify is received. In some examples, the computing device may store a plurality of default contrast scan protocols, and the user input may include a selection of one of the default contrast scan protocols. In other examples, the computing device may store one or more modified contrast scan protocols, and the user input may include a selection of one of the modified contrast scan protocols. In still further examples, the user input may include an indication that a new contrast scan protocol is to be defined. The contrast scan protocol may be a suitable contrast scan protocol, such as a CTP, a CTA followed by a CTP, a CTP followed by a CTA, a combined CTP and CTA, a CTA, or a another contrast scan. The contrast scan protocol may be specific to a particular anatomy and/or a particular suspected patient condition. For example, the contrast scan protocol may be specific to a head, head/neck, abdomen, heart, etc., and/or the contrast scan protocol may be specific to acute stroke, myocardial infarction, liver dysfunction, etc. Further, additionally or alternatively, the contrast scan protocol may be specific to a type of patient, such as pediatric, adult, advanced age adult, small, medium, large, etc. The user input may be received from a suitable user input device, such as the operator console 220 (which may include a keyboard, a mouse, a touchscreen, and/or another suitable input device).

At 304, an adaptive scan protocol graphical user interface (GUI) is displayed. The adaptive scan protocol GUI may be displayed on a display device communicatively coupled to the computing device, such as display 232. The adaptive scan protocol GUI may include one or more sections via which various parameters for the contrast scan protocol may be set/adjusted. Further, the adaptive scan protocol GUI may include a visual representation of the acquisition timings for the scan protocol that may change as the user enters input to adjust/set the scan parameters, as will be described in more detail below.

At 306, a number of scan zones that the contrast scan protocol is to be divided into is set based on user input to the adaptive scan protocol GUI. As explained above, the scan protocol may include different scan parameters that may be adjusted as the contrast scan progresses, such as temporal acquisition rate. To facilitate these adjustments, the contrast scan protocol may be divided into zones. The adaptive scan protocol GUI may include a plurality of user interface inputs, such as user interface elements, each representing a respective zone, and the user may select how many zones the contrast scan protocol is to include (e.g., 1-4 zones) by toggling one or more of the inputs. At 308, a temporal acquisition rate is set for each selected zone based on user input to the adaptive scan protocol GUI. For example, the adaptive scan protocol GUI may include a temporal acquisition rate value for each zone, and the user may adjust the temporal acquisition rate for one or more zones via input to the temporal acquisition rate inputs indicated at 526, 528 in FIG. 5.

At 310, additional scan parameters may be adjusted for each zone based on user input to the adaptive scan protocol GUI. The additional scan parameters may include x-ray source current and/or voltage, as indicated at 312. For example, when the imaging system is a CT system as described herein or another x-ray imaging system, the output of the x-ray source may be adjustable for each zone by the user. The adaptive scan protocol GUI may include a current input for each zone, and the x-ray source current for each zone may be adjusted by the user via input to the current inputs. In some examples, the additional scan parameters may include scan start/stop locations, as indicated at 314. In such examples, the adaptive scan protocol GUI may include start/stop location inputs for each zone, and the user may adjust the scan start/stop location for each zone, if desired. It is to be understood that the additional scan parameters discussed herein are exemplary, and other scan parameters may be adjusted without departing from the scope of this disclosure.

At 316, a respective, personalized timing for each selected zone is set based on user input to the adaptive scan protocol GUI. The timing may be event and/or time-based, as indicated at 318. Event-based timing may include timing based on the start of the scan, contrast agent response curve events (e.g., venous peak, arterial peak, contrast agent washout (also referred to venous return to baseline), or other curve triggers), contrast agent detection, proportion between two events, proportion relative to an event, group number, etc. Time-based timing may include delays or advances relative to specified events and/or time since the start of the scan. The adaptive scan protocol GUI may include a timing input for each zone as well as an event input for each zone. The user may set or adjust when each selected zone is to end by adjusting the respective timing and event inputs. For example, the timing input may be set in order to delay or advance a zone transition (where one zone ends and the next zone begins) by a specified amount of time relative to an event defined by selection of the corresponding event input. As a non-limiting example, a first zone may be specified as ending at a given time (e.g., 2 seconds) relative to an event (e.g., venous peak of the patient's contrast level curve) by setting the time of the timing input for the first zone and setting the event input of the first zone. The determination of whether the zone ends before or after the specified event may be based on whether positive or negative time is specified in the timing input. For example, positive time may indicate the zone is to end after the specified event while negative time may specify the zone is to end before the specified event. However, in some examples, an additional input may be present on the GUI which may be adjusted to specify before or after.

As explained above, the events that may be selected to trigger zone transitions may include events of a patient contrast level curve. A patient contrast level curve may be determined for a patient at the time the contrast scan is actually executed to image the patient. The patient contrast level curve may include an AIF curve, a tissue uptake curve (TUC), and/or a VOF curve. The AIF curve may represent the change in contrast level (after a contrast agent has been administered to the patient) at an artery of the patient, the TUC may represent the change in contrast level in a segmented tissue of the patient, such as the brain, and the VOF curve may represent the change in contrast level at a vein of the patient. Each patient may have a different contrast level curve (e.g., different peak timing, different peak height, different ascent knee length/slope, different descent knee length/slop, etc.). The contrast level curve for a patient may be measured during or before the contrast scan, depending on the scan protocol. If the contrast level curve is measured during the contrast scan, the patient contrast level curve may be estimated or extrapolated based on a short measured segment of the patient contrast level curve.

In this way, the adaptive scan protocol GUI may allow the lead technologist or other user to specify scan parameters that change during the contrast scan (including when the scan is complete) based on the patient's specific contrast agent kinetics, without knowing the patient's contrast agent kinetics ahead of time. As will be explained in more detail below, during execution of an adaptive scan protocol, the actual scan prescription that dictates the number and timing of passes/acquisitions of the imaging system (e.g., gantry rotations) and the settings for each acquisition (e.g., x-ray tube current) may be set based on the parameters defined by the scan protocol and adapted on the fly, automatically, when the imaged patient's contrast level curve is determined.

In examples where a secondary scan is performed with the primary contrast scan, such as a CTA performed within a CTP (where the CTA is the secondary scan), the number and/or timing of the phases/acquisitions of the secondary scan may be set based on user input to the adaptive scan protocol GUI, as indicated at 320. Similar to the zone selection and timing for the primary scan described above, the number of phases of the secondary scan may be selected via a phase selection input of the adaptive scan protocol GUI, and each selected phase may be given a timing (e.g., relative to a specified event) via timing inputs. If a secondary scan is not to be performed with the primary scan, a secondary scan input of the adaptive scan protocol GUI may be selected to an off position.

At 322, a fallback scan prescription may be set based on user input to the adaptive scan protocol GUI. As explained above, some scan protocols may include adjustments to scan parameters such as temporal acquisition rate as the scan progresses, and the timing of these adjustments may be based on patient-specific events that are detected in-flight (e.g., while the scan is progressing). If one or more of these events are not detected, the scan prescription that is executed based on the scan protocol may not function, or may not function as intended, which may impact diagnostic image quality. Thus, to prevent such issues should the events be undetectable, a fallback scan prescription may be set that may be executed if one or more specified events cannot be detected. The adaptive scan protocol GUI may include a fallback scan prescription section where the user may specify timing and parameters of the fallback scan prescription that are not event-based, such as temporal acquisition rate changes that occur at fixed times (e.g., relative to the start of the scan).

At 324, the information that is displayed via the adaptive scan protocol GUI may be updated as the user enters the user input described above. For example, when the user enters input adjusting a temporal acquisition rate for a particular zone, the temporal acquisition rate input for that zone may reflect the adjusted temporal acquisition rate. Further, the adaptive scan protocol GUI may include a preview section that displays a visual representation of the scan protocol, where a generic/base contrast agent curve (e.g., a VOF curve) is displayed and the timing of each scan acquisition of each zone is displayed as part of the curve. If a zone is turned on or off, if a zone transition time is adjusted, or if a temporal acquisition rate of a zone is adjusted, the preview section may be adjusted in a corresponding manner. Additional details of the adaptive scan protocol GUI, including adjustments to the preview section, are discussed below with respect to FIGS. 5 and 6.

At 326, the adaptive scan protocol is saved in memory when indicated (e.g., in response to a user input commanding the protocol be saved). The saving of the scan protocol may include saving any adjustments made to the scan protocol. The scan protocol may then be retrieved at a later time and executed in order to scan a patient according to the parameters specified in the scan protocol, as explained below with respect to FIG. 4.

FIG. 4 shows a flow chart illustrating a method 400 for performing a contrast scan according to an adaptive contrast scan protocol. Method 400 is described with respect to the system and components described above with respect to FIGS. 1-2 but could be carried out with other systems/components without departing from the scope of this disclosure. Method 400 may be carried out according to instructions stored in non-transitory memory of a computing device (e.g., computing device 216 of FIG. 2). Method 400 may include the execution of a scan protocol in order to image a patient, where the scan protocol may be an adaptive scan protocol defined/adjusted according to the method of FIG. 3. Thus, method 400 may be performed in response to authenticating an authorized operator, such as a lead technologist, a technologist, etc.

At 402, a user input specifying an adaptive scan protocol to execute is received. In some examples, the computing device may store a plurality of adaptive scan protocols, and the user input may include a selection of one of the adaptive scan protocols. The adaptive scan protocol may be a suitable contrast scan protocol, such as a CTP, a CTA followed by a CTP, a CTP followed by a CTA, a combined CTP and CTA, a CTA, or a another contrast scan protocol. The selected scan protocol may be specific to a particular anatomy, a particular suspected patient condition, and/or a type of patient. The user input may be received from a suitable user input device, such as the operator console 220 (which may include a keyboard, a mouse, a touchscreen, and/or another suitable input device). In some examples, the selected scan protocol may be a scan protocol that is set/defined/adjusted according to method 300 described above. Further, in some examples, the operator may enter a user input indicating that the scan protocol is to be executed (e.g., as opposed to modified). In other examples, the scan protocol may be executed automatically in response to the user selecting the scan protocol.

At 404, the operator may be prompted to perform a scout scan of an imaging subject via a run-time graphical user interface (GUI). The scout scan may include a low-resolution scan that generates 2-dimensional images of the imaging subject from which the scan range/field of view of the following diagnostic scan may be set. In some examples, a notification prompting the user to perform the scout scan may be displayed as part of a run-time GUI, and the scout scan may be performed in response to a user input commanding the scout scan be executed. The run-time GUI may be displayed on a suitable display device associated with the imaging system, such as display 232. The run-time GUI may present scan information to the operator of the imaging system, such as patient information, scan parameter settings, dose information, etc., as will be explained in more detail below. In other examples, the user may command the imaging system to perform the scout scan without the imaging system prompting the user to perform the scout scan, or the scout scan may be performed automatically. In still further examples, no scout scan may be performed.

At 406, a diagnostic scan range may be set via the run-time GUI. For example, the image(s) generated from the scout scan may be displayed via the run-time GUI along with one or more scan range overlays. The user may adjust the extent of the scan range overlays to set the diagnostic scan range. At 408, some or all of the adaptive scan protocol GUI may be displayed within or along with the run-time GUI. Via the adaptive scan protocol GUI, the operator may view the set scan parameters for the selected scan protocol. In some examples, the operator may adjust the set scan parameters for the current scan via the adaptive scan protocol GUI, in the same manner as discussed above with respect to FIG. 3. However, if the operator adjusts any of the scan parameters, the adjustments may not be saved. In this way, one-time adjustments to the scan protocol may be made by the operator of the imaging system during a current scan, but the selected scan protocol may not be adjusted for subsequent scans.

At 410, method 400 determines if a user input requesting to import patient data has been received. The user input may be received via the run-time GUI. For example, the run-time GUI may include an import input that when selected by the operator causes the patient data to be imported. The patient data may include a previously measured and/or estimated AIF curve, VOF curve, and/or tissue uptake curve, measured and/or estimated during a prior contrast scan (e.g., a contrast scan immediately preceding the current contrast scan) or during a prior timing bolus event. In other examples, the patient data may include external sensor data from a blood flow sensor or other suitable sensor data. In some embodiments, when patient data is available, the patient data may be imported/available automatically and explicit user input may not be needed in order for the patient data to be used during execution of the current scan protocol.

If a user input has been received requesting to import patient data, method 400 proceeds to 412 to import the patient data. If a user input requested to import patient data has not been received, method 400 proceeds to 414 to perform one or more acquisitions according to a scan prescription that is generated according to the selected scan protocol. The one or more acquisitions may be commenced once a contrast agent has been injected (and after a prep delay following the contrast agent injection). As a non-limiting example, the contrast agent may comprise iodine. As other examples, the contrast agent may comprise an ionic contrast medium such as meglucamine diatriozoate, or a non-ionic contrast medium such as iopromide or ohexol. The contrast agent may be intravenously injected using either automatic or manual methods. In some examples, such as when the contrast agent is injected manually (e.g., by the operator or another clinician), the operator may enter a user input indicating the contrast agent has been injected (which may notify the imaging system of when to begin acquisitions). Further, while not included in FIG. 4, some scan protocols may include a non-contrast scan of the intended/target anatomy, which may be performed before the injection of the contrast agent.

The scan prescription may include the number and timing of each acquisition, the system settings for each acquisition (e.g., x-ray source current and voltage), the scan range (e.g., scan stop and start locations) for each acquisition, table position for each acquisition, etc. As used herein, a scan acquisition or pass may refer to a full gantry rotation (e.g., when the brain is being imaged) or a partial gantry rotation (e.g., when the heart is being imaged). In either case, an acquisition or pass may include the amount of gantry rotation that is needed to obtain the desired views for the anatomy/scanning protocol.

The scan prescription may be determined from the scan parameters defined in the selected scan protocol. For example, the scan prescription may dictate that acquisitions are to be carried out once every 2 seconds for the first zone and then once every 3.4 seconds for the second zone, with the transition from the first zone to the second zone occurring 2 seconds after the peak of the VOF curve (referred to as the venous peak). In examples where patient data is imported or otherwise available before the contrast scan acquisitions begin, the scan prescription may be adjusted based on the patient data. As explained above with respect to FIG. 3, various zones and/or phases of the scan protocol may start or end based on patient specific events, such as the peak of the patient's VOF curve or once the contrast agent has washed out of the patient. The patient data may inform on when these events will occur relative to the start of the contrast scan. For example, the patient data may include a VOF curve for the patient that was measured during a prior contrast scan. The elapsed amount of time from contrast agent injection until the peak of the VOF curve and the elapsed amount of time from contrast agent injection until the return to baseline of the VOF curve may be determined and these times may be used to adjust the scan prescription. As an example, if the selected scan protocol indicates that the first zone of the scan is to end 2 seconds after the VOF peak, the scan prescription may be updated so that the first zone ends 2 seconds after the determined time of the VOF peak (e.g., if the patient data indicates that the VOF peak will occur 35 seconds after contrast agent injection, the scan prescription may be updated so that the first zone ends at 37 seconds after contrast agent injection).

However, if the patient data is not available when the acquisitions commence, the patient data may be determined from the initial acquisitions of the contrast scan. For example, the contrast level of a specified anatomical feature (e.g., an artery) may be measured during the initial acquisitions of the contrast scan and plotted as a function of time. After a predetermined amount of time, or once a peak of a curve formed by the plotted contrast levels (or other suitable event) is detected, the measured segment of the curve may be used to predict when subsequent events are going to occur (e.g., venous peak and venous return to baseline), and the scan prescription may be updated on the fly based on the predicted time of these events. In some examples, these initial acquisitions may be of a different anatomical feature than the anatomy intended to be imaged in the diagnostic scan, and thus once the curve segment has been measured, the table supporting the imaging subject may be automatically moved to center the intended anatomy in the imaging system.

At 416, a notification of the scan progress is displayed via the run-time GUI. For example, the run-time GUI may include a visual indicator of the scan progress that may change as the scan progresses. The visual indicator may include one or more progress bars, which may indicate scan progression by progressively changing in color or brightness over time (e.g., from left to right across the progress bar), and may include relative timing of each acquisition and time between each acquisition. At 418, a confirmation of the adjusted scan prescription (adjusted based on the imported data or monitored contrast level curve) may be displayed via the run-time GUI. For example, after the scan prescription is adjusted, a visual representation of the scan prescription may be displayed as part of the run-time GUI, with the visual representation showing the patient's contrast level curve and with the timing of individual acquisitions as dictated by the scan prescription shown as part of the contrast level curve. At 420, a notification may displayed via the run-time GUI once the scan is complete. Additional details about the run-time GUI are provided below with respect to FIG. 7.

At 422, one or more reconstructed images are displayed and/or stored. For example, one or more diagnostic images may be reconstructed from the data acquired during the contrast scan using known reconstruction techniques, such as filtered back projection or iterative reconstruction. The one or more diagnostic images may be output to a display device (e.g., display device 232) for display to an operator or a physician, to a storage medium (e.g., mass storage 218) for retrieving at a later time, and so on. Method 400 may then end.

While method 400 is described above as being implemented on the same computing device as method 300 described above, in some examples method 300 may be implemented on a separate computing device, such as an edge device, a cloud computing system, a server, etc. In such examples, the adaptive scan protocol GUI may be displayed, during execution of method 300, on a display device associated with the separate computing device. When method 400 is executed, the selected adaptive scan protocol may be sent from the separate computing device to the computing device executing method 400. Such a configuration may allow a lead technologist to set adaptive scan protocol settings on one separate computing device, and those protocols may be sent out to multiple, separate imaging systems in communication with the separate computing device.

Further, in some examples, two or more contrast scans may be performed back-to-back. For example, a CTA may be performed immediately after a CTP, or vice versa. In such examples, after the notification is output via the run-time GUI informing the operator that the current contrast scan is complete, method 400 may return to 414 to perform the second contrast scan. In such examples, the run-time GUI may display a notification instructing the operator to perform a second contrast agent injection, and this notification may be displayed at a time that is based on the patient contrast level curve determined during the prior contrast scan (e.g., at the venous return to baseline of the prior contrast agent injection).

FIG. 5 shows an example adaptive scan protocol GUI 500 that may be displayed on a display device (e.g., display 232) in response to a user request to modify an existing adaptive scan protocol or in response to a user request to establish anew adaptive scan protocol. Adaptive scan protocol GUI 500 is a non-limiting example of the adaptive scan protocol GUI that is displayed as part of method 300 of FIG. 3. The adaptive scan protocol GUI 500 shown in FIG. 5 is specific to a head perfusion and multi-phase angiography scan protocol (e.g., a mCTA-in-CTP), but it is to be understood that a similar adaptive scan protocol GUI may be displayed in order to set parameters for other types of contrast scans. GUI 500 includes a preview section 501. The preview section 501 includes a generic contrast level curve 502. The generic contrast level curve 502 may have an envelope that mimics a generic (e.g., non-patient specific) VOF curve or other suitable contrast level curve (e.g., an AIF curve or a TUC). The generic contrast level curve may be based on an average VOF curve for a plurality of patients, at least in some examples. The contrast level curve 502 is formed by a plurality of sample acquisition bars, such as sample acquisition bar 503, that represent when each acquisition of the perfusion scan is timed to occur according to the scan protocol as defined by the user via a perfusion section 520 of the GUI 500. The preview section 501 further includes a plurality of angiography phase lines, such as phase line 512. The phase lines may be placed over the contrast level curve 502 at the times specified by the scan protocol as defined by the user via a CTA section 550.

The perfusion section 520 includes a plurality of user interface control inputs via which the user may define how many zones the perfusion scan is to be divided into, set values for one or more scan parameters for each zone, and set the timing of when each zone is to occur. Thus, the perfusion section 520 includes a plurality of zone inputs 522, such as zone 1 input 524, and each zone has a respective zone input. The zone inputs may be inputs that, via user input to the respective inputs, may select or deselect each zone. For example, as shown in FIG. 5, each zone input is selected to the on position, and as such the perfusion scan portion of the scan protocol is divided into four zones. While four possible zones are shown in FIG. 5, it is to be understood that more or fewer zones may be presented via the perfusion section 520 without departing from the scope of this disclosure.

The perfusion section 520 further includes a plurality of temporal acquisition rate inputs 526, a plurality of parameter inputs 532, a plurality of timing inputs 534, and a plurality of event inputs 538. The plurality of temporal acquisition rate inputs 526 includes one temporal acquisition rate input for each zone (and hence as shown includes four inputs). For example, the plurality of temporal acquisition rate inputs 526 includes a temporal acquisition rate input 528 for zone 1. Via each respective temporal acquisition rate input, the user may specify the temporal acquisition rate for each selected zone. For example, temporal acquisition rate input 528 includes a temporal acquisition rate value (shown as 2 seconds) that may be adjusted via user input to the adjacent arrow inputs. Selection of an arrow input may result in the temporal acquisition rate value incrementing up or down by a predetermined value, such as 0.1 s per click/selection of an arrow input. In some examples, the user may directly enter a temporal acquisition rate value rather than change the temporal acquisition rate value via the arrow inputs.

The plurality of parameter inputs 530 includes one parameter input for each zone. For example, the plurality of parameter inputs 530 includes a parameter input 532 for zone 1. Via each respective parameter input, the user may specify values for a given scan parameter for each selected zone. In the example shown in FIG. 5, the scan parameter that is defined by the plurality of parameter inputs 530 is x-ray source (e.g., x-ray tube) current, but other scan parameters are possible, such as x-ray source voltage, scan start/stop locations, etc. Further, more than one scan parameter may be defined via the perfusion section 520; for example, a second plurality of parameter inputs may be provided via which the user may set the x-ray source voltage or another parameter for each selected zone. As shown, the user may directly enter a scan parameter value (e.g., 200 mA) to each parameter input, but other mechanisms for adjusting or setting a scan parameter value are possible, such as selection from a drop-down menu, arrow inputs, etc.

The plurality of timing inputs 534 includes one timing input for each zone. For example, the plurality of timing inputs 534 includes a timing input 536 for zone 1. Via each respective timing input, the user may specify the end time for each selected zone, where that zone transitions to the next zone. As shown, the user may directly enter a time value (e.g., 2 seconds) to each timing input, but other mechanisms for adjusting or setting a timing value are possible, such as selection from a drop-down menu, arrow inputs, etc. The time values entered may be positive or negative, which may affect whether the zone ends before or after an event specified by the corresponding event input, as described below.

The plurality of event inputs 538 includes one event input for each zone. For example, the plurality of event inputs 538 includes an event input 540 for zone 1. Via each respective event input, the user may specify an event that triggers the end of each selected zone, where that zone transitions to the next zone (with the time value specified in the corresponding timing input indicating when relative to the event the zone is to end). As shown, the user may select an event from a drop-down menu, but other mechanisms for specifying an event are possible, such as the user directly entering the event. The events available for selection in the drop-down menu may include venous peak, contrast agent washout, arterial peak, tissue uptake peak, other contrast level curve events (such as ascent or decent knees), start of scan, and/or other events.

In GUI 500, the timing of when each selected zone is to end is by default set to be after the event specified in the corresponding event input. For example, zone 1 is set in the example of GUI 500 shown in FIG. 5 to end 2 seconds after venous peak. However, a zone may be set to end before the specified event if the time value entered into the corresponding timing input is entered as a negative value rather than a positive value. For example, if the user were to enter −2 as the value for the timing input 536, the first zone would end 2 seconds before the venous peak.

CTA section 550 includes a selection input 552 which the user may select on or off to include or not include a CTA in the scan protocol. In GUI 500, the CTA is a virtual mCTA where acquisitions that are performed as part of the perfusion scan are selected and (at least in some examples) differentially processed/reconstructed to generate CTA images in addition to the CTP images. However, in some examples, GUI 500 may include, additionally or alternatively, a physical CTA section where scan parameters may be set for CTA acquisitions that are different or separate from the CTP acquisitions.

When the selection input 552 is selected to the on position (as shown), various user interface control inputs may be become active to allow the user to set parameters of the CTA. These inputs include a phase selection input 554, via which the user may set how many phases the mCTA is to include (shown here as 1-3 phases, but more or fewer are possible). Each phase has an associated set of timing inputs. For example, phase 1 has an event input 556 and a timing input 558 that function similarly to the timing and event inputs of the perfusion section. Via the event inputs, the user may specify an event for each selected phase, and via the timing inputs, the user may specify a timing relative to the corresponding event for each selected phase.

Accordingly, the scan protocol that is defined by GUI 500 shown in FIG. 5 includes a perfusion scan and a virtual mCTA within the perfusion scan. The perfusion scan is divided into four zones. The first zone may commence at a default time (e.g., after a prep delay following contrast agent injection) that is determined automatically by the computing device and is not specified by the adaptive scan protocol set by the user via GUI 500. The first zone may have a temporal acquisition rate of once every 2 seconds and may end 2 seconds after the patient's measured or estimated venous peak. The second zone may begin when the first zone ends and may have a temporal acquisition rate of once every 3 seconds. The second zone may end (and the third zone may begin) 10 seconds after the patient's venous peak. The third zone may have a temporal acquisition rate of once every 4 seconds and may end 10 seconds after washout (e.g., the patient's venous return to baseline). The fourth zone may have a temporal acquisition rate of once every six seconds and may end 30 seconds after washout. The mCTA includes three phases, a first phase at 2 seconds after venous peak, a second phase at 8 seconds after venous peak, and a third phase at 16 seconds after venous peak.

The preview section 501 may include visual information to convey the selected zones, temporal acquisition rates, and CTA phases. For example, the preview section 501 includes a visual representation of the scan protocol that includes the contrast level curve 502, which has a visual appearance that reflects the number of selected zones and the selected temporal acquisition rate for each selected zone of the perfusion scan. As shown, contrast level curve 502 is divided into four zones, due to each of the four zones being selected in the perfusion section 520. The temporal acquisition rate of each zone is reflected in the contrast level curve 502 by how many sample acquisition bars are included in each zone of the contrast level curve 502. Accordingly, the contrast level curve 502 is divided into four zones, a first zone 504, a second zone 506, a third zone 508, and a fourth zone 510. Each zone may have a different visual appearance, such as a different color or pattern for the acquisition bars of that zone. Each zone has a different temporal acquisition rate and thus the contrast level curve 502 includes acquisition bars that are spaced apart by different amounts for each zone. For example, the first zone 504 includes a first, faster temporal acquisition rate (e.g., once every 2 seconds) and the second zone 506 includes a second temporal acquisition rate that is slower than the first temporal acquisition rate (e.g., once every 3 seconds). Thus, the first zone 504 includes acquisition bars that are spaced apart by a smaller amount that the acquisition bars of the second zone 506.

Each zone of the perfusion scan and each phase of the angiography scan may be timed to occur based on patient specific events, such as the start of the scan/contrast agent injection, venous peak, and washout (also referred to as venous return to baseline). The zone transitions and phase lines of the preview section 501 may be positioned relative to corresponding events of the generic contrast level curve 502. For example, the transition from the first zone to the second zone is timed to occur 2 seconds after the venous peak, and thus the second zone 506 may begin just after the peak of the contrast level curve 502. In this way, the lead technologist or other user who is setting the scan parameters for the selected scan protocol may see a somewhat realistic representation of how the scan acquisitions will progress when the scan protocol is actually executed. As will be shown in FIG. 6 (described below), the information shown in the preview section 501 may change as certain scan parameters are adjusted.

Thus, the visual representation of the scan protocol may include a plurality of acquisition bars that each have a respective height that is selected to form an envelope (e.g., a curve formed by the top of each acquisition bar) that matches a generic or average patient contrast level curve. Further, the plurality of acquisition bars are distributed based on the defined number of zones and the temporal acquisition rate for each zone. The visual representation may further include one or more phase lines that represent when secondary scan (e.g., mCTA) phases are timed to occur relative to the acquisitions of the primary (e.g., perfusion) scan and the patient contrast level curve.

FIG. 6 shows GUI 500 in an adjusted state 600 where the user has adjusted some of the parameters of the scan protocol relative to GUI 500 shown in FIG. 5. Specifically, the user has only selected two zones rather than four zones. Thus, zone 1 input 524 is in the on position, a zone 2 input 606 is in the on position, a zone 3 input 608 is in the off position, and a zone 4 input 610 is in the off position. As a result of zones 3 and 4 not being selected, the temporal acquisition rate, parameter, timing, and event inputs for zones 3 and 4 are blank/not Tillable. For example, a temporal acquisition rate input 612 for zone 3 does not include a temporal acquisition rate value and the user may be prevented from entering a temporal acquisition rate value to temporal acquisition rate input 612. Additionally, the timing of the first zone has been adjusted to end at 8 seconds after venous peak, and the timing of the second zone has been adjusted to end 20 seconds after washout.

The preview section 501 is updated to reflect the change in the number of selected zones and timing of the selected zones. The contrast level curve 502 is divided into only a first zone 602 and a second zone 604. The first zone 602 now extends later than the first zone of FIG. 5 (e.g., to 8 seconds after the venous peak rather than 2 seconds). Because the scan protocol only includes two zones for the perfusion scan, the second zone 604 now extends until the scan ends. Thus, the plurality of acquisition bars each have a respective height that is selected to form the envelope that matches the generic patient contrast level curve, but the distribution (and number) of the acquisition bars has changed due to the change in the number and timing of the zones.

While GUI 500 includes a perfusion section and a CTA section, where the CTA can be activated or deactivated, other configurations for the adaptive scan protocol GUI are possible. For example, the perfusion section may include an activation input, similar to the CTA section. If the perfusion scan is not selected, the user may specify parameters for the CTA section, which may result in only the CTA scan being performed when the scan protocol is executed. Further, two or more scan protocols may be linked in order to perform back-to-back contrast scans. As an example, if a CTA is to be performed after a CTP (rather than during), the scan protocol for the CTP scan may be set as described above, with the CTA being deactivated. Then, the user may specify via the adaptive scan protocol GUI or another GUI that a second adaptive scan protocol is to be performed upon completion of the first adaptive scan protocol, with the second adaptive scan protocol defined as explained above (e.g., CTA parameters may be set and the CTP may be deactivated).

FIG. 7 shows an example run-time GUI 700 that may be displayed on a display device (e.g., display 232) in response to a user request to execute an existing adaptive scan protocol. Run-time GUI 700 is a non-limiting example of the run-time GUI that is displayed as part of method 400 of FIG. 4.

Run-time GUI 700 includes a personalized scan prescription section 702 where a visual representation of the scan prescription for the imaging subject (e.g., patient) is displayed. The scan prescription may be generated based on the selected adaptive scan protocol and, in some examples, contrast level curve information for the patient. The run-time GUI 700 also includes a first progress bar 720 and a second progress bar 722 that each display the current status/progress of the contrast scan. Additionally, the run-time GUI 700 may include a patient information section 730, a scan information section 740, a scan range selection section 750, and a dose information section 760.

In the patient information section 730, information about the imaging subject may be displayed, such as a patient name and/or ID number, patient gender, and patient position (e.g., head first/supine). In the scan information section 740, information about the scan protocol may be displayed, such as the name of the scan protocol and the sequences of the scan protocol (e.g., the scout scan, the non-contrast scan, and contrast scan or scans, which as shown in FIG. 7 includes an mCTA in CTP). Additionally, when a sequence of the scan protocol is completed, a checkmark or other visual indicator may be displayed. The current sequence may be highlighted or otherwise visually indicated. In the scan range selection section 750, scout images of the imaging subject may be displayed with the current scan range displayed as an overlay on the scout image(s). The scan range may be adjusted by resizing the overlay(s). In the dose information section 760, information about the x-ray radiation dose administered to the imaging subject may be displayed, such as projected dose, total accumulated dose, etc., so that the operator of the imaging system may monitor the patient's x-ray radiation exposure.

While not shown in FIG. 7, the run-time GUI 700 may initially display a replicate of the adaptive scan protocol GUI (e.g., as shown in FIGS. 5 and 6) so that the operator is given the opportunity to confirm the settings for the current adaptive scan protocol, and if desired, change any of the settings. As an example, the operator may decide to extend the duration of the final scanning zone to ensure that sufficient acquisitions are taken at and after the subject's venous return to baseline. Some patients, such as patients with atrial fibrillation or patients that are over the age of 80, may have relatively long venous descent times, and thus contrast agent washout may occur later for these patients than other patients. Thus, the operator may conclude that the adaptive scan protocol ends too early for the subject if the subject is over 80 or the operator knows the subject has atrial fibrillation, and the operator may extend the scanning duration for that subject. Further, the run-time GUI may include one or more user interface inputs that, when selected by the operator, confirm the scan protocol setting and/or trigger the start of the contrast scan. Once the contrast scan has begun, the scan prescription section 702 may be displayed.

The scan prescription section 702 may include a contrast level curve 704 that is similar to the contrast level curve 502 of GUI 500. The contrast level curve 704 may be divided into zones according to the scan protocol; as shown, the contrast level curve 704 includes a first zone 706 and a second zone 708, with the first zone having a first, higher temporal acquisition rate and the second zone having a second, lower temporal acquisition rate. The scan prescription section 702 also includes the CTA phase lines, such as phase line 710, to indicate where the CTA phases are timed to occur. The scan prescription section 702 also includes a starting point 712 that is timed at the end of the prep delay and indicates when the acquisitions of the scan commence.

While the contrast level curve 704 shown in FIG. 7 is the same generic contrast level curve shown in the adaptive scan protocol GUI, it is to be understood that at least in some examples, the run-time GUI 700 may display a visual representation of the scan prescription that has been generated based on the patient's actual contrast level curve, and thus the visual representation of the scan prescription may include the plurality of acquisition bars each having a respective height that is selected to form an envelope that matches the determined contrast level curve of the patient being imaged. An example envelope of a personalized patient-specific contrast level curve 714 is shown in FIG. 7. When displayed, the personalized contrast level curve 714 may include acquisition bars that are distributed according to the scan prescription, as explained above with respect to FIGS. 5 and 6. However, instead of being positioned relative to events of the generic curve, the acquisition bars may be positioned relative to events of the personalized contrast level curve. For example, the more tightly placed acquisition bars of the first zone may extend until after the peak of the personalized contrast level curve 714, and the CTA phase lines may be shifted to the right, as the peak of the personalized contrast level curve 714 may be later than the peak of the generic contrast level curve 704.

The personalized contrast level curve 714 may be generated based on patient contrast level information, which may be obtained from a prior contrast scan, a timing bolus carried out before the current contrast scan, or during the current contrast scan. When the patient contrast level information is obtained in-flight during the current contrast scan, the personalized contrast level curve may be generated once a certain number of acquisitions have been obtained and/or a certain point of the contrast agent uptake or washout has been reached. Thus, during at least a first portion of the contrast scan, the generic contrast level curve may be displayed. Once the personalized contrast level curve is generated, the personalized contrast level curve may replace the generic curve. In another example, the scan prescription section 702 may initially display a fallback scan prescription, which may be based on the fallback scan protocol as described above, and may not be based on patient information. Then, once the personalized contrast level curve is generated, the fallback scan prescription may be replaced with the personalized contrast level curve.

As the contrast scan progresses, the first progress bar 720 and the second progress bar 722 may change in visual appearance. For example, the first progress bar 720 may represent the first zone of the perfusion scan and may include a waveform, with each raised segment of the waveform representing an acquisition. As the scan progresses, the color of the waveform may progressively change, e.g., turning gray to blue from left to right, in sync with the scan progress. The second progress bar 722 may represent the second zone and may include a waveform with the raised portions of the waveform representing the acquisitions. Once the first zone of the scan is completed, the entire waveform of the first progress bar 720 may be the different color (e.g., blue) and color of the second progress bar 722 may progressively change in sync with the scan progression. However, in other examples, the first progress bar 720 may represent the entire perfusion scan and the second progress bar 722 may represent the acquisitions of the angiography scan.

As explained above, the personalized contrast level curve may be based on measured patient contrast level information, but at least a portion of the personalized contrast level curve may be estimated or extrapolated from the measured segment of the curve. In some examples, when the acquisitions are complete and as projection data is sent for image reconstruction/post-processing, the actual contrast level curve may be generated as a first step to the perfusion map computation. In some examples, a post-scan workflow may include displaying to the operator a comparison of the estimated contrast level curve used to generate the scan prescription vs the actual measured contrast level curve. The differences between the estimated and measured curves may be used to inform the operator of the accuracy of the curve estimates, inform the operator of any errors in the estimates that might have impacted diagnostic image quality, and/or update the curve estimation models.

Thus, the systems and methods disclosed herein provide for workflows for setting adaptive scan protocols and then executing the adaptive scan protocols, with each workflow including a graphical user interface via which a respective user (e.g., lead technologist and then scanning technologist) may adjust/set and then carry out an adaptive scan protocol. The adaptive scan protocol GUI described herein may allow a lead technologist or another supervising clinician/personnel to quickly set parameters for the scan protocol based on patient events that will be determined at the time of scanning. The adaptive scan protocol GUI may provide the user with a limited set of options for setting the parameters for the scan protocol, such as a limited number of zones (e.g., 1-4 or other suitable range, such as 1-5 or 1-6 zones), a limited set of scan parameters that can be adjusted for each zone (such as temporal acquisition rate and x-ray source current), a limited set of secondary scan phases, and a limited set of events that can trigger the end of each zone and/or a secondary scan phase. In doing so, user interaction with the computing device to set the adaptive scan protocol may be reduced, thereby making the user's workflow more efficient. Further, consistency may be increased all adaptive scan protocols.

Then, when an operator (e.g., the lead technologist or a scanning technologist) selects the adaptive scan protocol for executing a contrast scan on a patient, the parameters set by the adaptive scan protocol may be used to automatically set the scan prescription for the contrast scan. The operator, at the time of scanning, may view visual representations (e.g., via a run-time GUI) of the scan prescription, scan settings, and scan progress. Further, via the run-time GUI, the visual representation of the scan prescription may be adapted based on the timing of the events that are specific to the patient being imaged, even before the events occur. In doing so, the user may quickly assess the progress of the scan and determine any potential image quality issues before the images have been reconstructed, which may expedite patient diagnosis and increase scanning efficiency. Further, by eliminating or reducing scan-time parameter adjustments, scan consistency across patients may be improved and the cognitive load on the scan technologist/system operator may be reduced, which may increase diagnostic image quality and improve patient outcomes.

A technical effect of the disclosure is that an adaptive contrast scan may be defined and performed based on patient specific events, which may increase diagnostic image quality and/or reduce user workflow demands.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a computing device communicatively coupled to an imaging system, the method comprising:
    selecting a scan protocol;
    displaying an adaptive scan protocol graphical user interface (GUI) on a display device coupled to the computing device;
    adjusting one or more parameters of the scan protocol in response to user input to the adaptive scan protocol GUI;
    updating a visual representation of the scan protocol displayed via the adaptive scan protocol GUI in correspondence to the adjustment of the one or more parameters of the scan protocol; and
    storing the adjusted scan protocol in memory of the computing device; then
    retrieving the adjusted scan protocol at a later time and executing the adjusted scan protocol to scan a patient, wherein the scan protocol is a scan protocol for a perfusion scan, wherein the visual representation of the scan protocol includes a plurality of acquisition bars each having a respective height selected to form an envelope that matches a generic patient contrast level curve, and wherein the plurality of acquisition bars are distributed based on a temporal acquisition rate of each selected zone of the scan protocol.

2. The method of claim 1, wherein executing the adjusted scan protocol includes setting a scan prescription for the imaging system based on the adjusted scan protocol and a contrast level curve of the patient and performing one or more acquisitions with the imaging system according to the scan prescription.

3. The method of claim 2, further comprising displaying, on the display device, a run-time GUI in response to a request to execute the adjusted scan protocol, the run-time GUI including a visual representation of the scan prescription.

4. The method of claim 1, wherein a timing of one or more selected zones in response to user input to the adaptive scan protocol GUI, wherein the timing is event-based and time-based.

5. The method of claim 1, wherein adjusting the one or more parameters of the scan protocol comprises adjusting a number of selected zones of the scan protocol, a temporal acquisition rate of one or more selected zones, and/or a timing of one or more selected zones in response to user input to the adaptive scan protocol GUI,
wherein adjusting the number of selected zones of the scan protocol, the temporal acquisition rate of one or more selected zones, and/or the timing of one or more selected zones in response to user input to the adaptive scan protocol GUI comprises:
displaying, via the adaptive scan protocol GUI, a respective timing input for each selected zone and a respective event input for each selected zone; and
adjusting the timing of a selected zone by adjusting a time value of the respective timing input for that selected zone and/or adjusting a selected event of the respective event input for that selected zone.

6. The method of claim 5, wherein the respective event input includes a drop-down menu including a plurality of possible events, the plurality of possible events including a scan start, a venous peak of a patient contrast level curve, and a washout of the patient contrast level curve.

7. The method of claim 1, wherein updating the visual representation of the scan protocol displayed via the adaptive scan protocol GUI in correspondence to the adjustment of the one or more parameters of the scan protocol comprises updating the distribution of the plurality of acquisition bars in response to an adjustment to a temporal acquisition rate of a selected zone.

8. The method of claim 1, wherein updating the visual representation of the scan protocol displayed via the adaptive scan protocol GUI in correspondence to the adjustment of the one or more parameters of the scan protocol comprises updating the distribution of the plurality of acquisition bars in response to an adjustment to a timing of a selected zone.

9. The method of claim 1, wherein adjusting one or more parameters of the scan protocol in response to user input to the adaptive scan protocol GUI comprises adjusting a number and/or a timing of one or phases of an angiography scan to be performed with the perfusion scan, and wherein adjusting the visual representation comprises adjusting a number and/or a position of one or more phase lines overlaid on the plurality of acquisition bars in correspondence to the adjustment to the number and/or the timing of the one or phases of the angiography scan.

10. A method for a computing device communicatively coupled to an imaging system, the method comprising:

adjusting one or more parameters of a scan protocol in response to user input to an adaptive scan protocol GUI; and
updating a visual representation of the scan protocol displayed via the adaptive scan protocol GUI in correspondence to the adjustment of the one or more parameters of the scan protocol; then
retrieving the adjusted scan protocol at a later time and executing the adjusted scan protocol to scan a patient by setting a scan prescription for imaging the patient with the imaging system based on the adjusted scan protocol and a contrast level curve of the patient,
displaying, on a display device coupled to the computing device, a run-time graphical user interface (GUI), the run-time GUI including a visual representation of the scan prescription, and
performing one or more acquisitions with the imaging system according to the scan prescription,
wherein the visual representation of the scan prescription comprises a plurality of acquisition bars each having a respective height selected to form an envelope that matches a patient contrast level curve, and wherein the plurality of acquisition bars are distributed based on a respective temporal acquisition rate of each of one or more zones of the scan protocol.

11. The method of claim 10, wherein the patient contrast level curve is generated after at least one acquisition of the one or more acquisitions has been performed, wherein the scan prescription is set once the patient contrast level is generated, and wherein the visual representation is displayed once the patient contrast level is generated.

12. The method of claim 10, further comprising displaying, via the run-time GUI, a scan acquisition bar that progressively notifies of a current status of the scan prescription.

13. A system, comprising:
a display device;
a non-transitory memory storing instructions; and
a processor configured to execute the instructions to:
select a scan protocol;
display, on the display device, an adaptive scan protocol graphical user interface (GUI);
adjust one or more parameters of the scan protocol in response to user input to the adaptive scan protocol GUI;
update a visual representation of the scan protocol displayed via the adaptive scan protocol GUI in correspondence to the adjustment of the one or more parameters of the scan protocol; and
store the adjusted scan protocol in the non-transitory memory; then
retrieve the adjusted scan protocol at a later time and execute the adjusted scan protocol to scan a patient by displaying, on the display device, a run-time GUI including a visual representation of a scan prescription generated based on the adjusted scan protocol, and
commanding an imaging system to perform one or more acquisitions according to the scan prescription,
wherein the visual representation of the scan protocol displayed via the adaptive scan protocol GUI includes a first plurality of acquisition bars each having a respective height selected to form a first envelope that matches a generic contrast level curve, and wherein the visual representation of a scan prescription displayed via the run-time GUI includes a second plurality of acquisition bars each having a respective height selected to form a second envelope that matches a contrast level curve of the patient.

14. The system of claim 13, wherein the one or more parameters of the scan protocol comprise a number of selected zones, a temporal acquisition rate of one or more selected zones, and/or a timing of one or more selected zones.

15. The system of claim 14, wherein the timing of each selected zone is relative to one or more events.

16. The system of claim 15, wherein the one or more events including a start of scanning, a venous peak of a patient contrast level curve, and a washout of the patient contrast level curve.

17. The system of claim 13, wherein the first plurality of acquisition bars are distributed based on one or more temporal acquisition rates specified by the adjusted scan protocol, and wherein the second plurality of acquisition bars are distributed based on one or more temporal acquisition rates specified by the scan prescription.

* * * * *